United States Patent [19]

Scholl

[11] Patent Number: 5,258,508

[45] Date of Patent: Nov. 2, 1993

[54] PROCESS FOR THE PREPARATION OF OLIGOMERIC POLYISOCYANATES AND THEIR USE

[75] Inventor: Hans-Joachim Scholl, Cologne, Fed. Rep. of Germany

[73] Assignee: Bayer Aktiengesellschift, Leverkusen, Fed. Rep. of Germany

[21] Appl. No.: 893,866

[22] Filed: Jun. 5, 1992

[30] Foreign Application Priority Data

Jun. 15, 1991 [DE] Fed. Rep. of Germany ....... 4119753

[51] Int. Cl.$^5$ .................... C07D 229/00; C08G 18/28
[52] U.S. Cl. ...................... 540/202; 528/45; 528/67; 528/73
[58] Field of Search ............ 528/45, 67, 73; 540/202; 544/193; 556/428

[56] References Cited

U.S. PATENT DOCUMENTS

| | | | |
|---|---|---|---|
| 4,476,054 | 10/1984 | Disteldorf et al. | 260/239 A |
| 4,595,534 | 6/1986 | Scholl | 260/239 A |
| 4,614,785 | 9/1986 | Richter et al. | 528/45 |
| 4,912,210 | 3/1990 | Disteldorf et al. | 540/202 |
| 4,994,541 | 2/1991 | Dell et al. | 528/51 |
| 5,043,092 | 8/1991 | Pedain et al. | 252/182.21 |

FOREIGN PATENT DOCUMENTS 1153815 5/1969 United Kingdom .

OTHER PUBLICATIONS

A. Farkas and G. A. Mils, Adv. Catal. 13, pp. 393 et seq (1962).

*Primary Examiner*—Mukund J. Shah
*Assistant Examiner*—Y. N. Gupta
*Attorney, Agent, or Firm*—Joseph C. Gil; Richard E. L. Henderson

[57] ABSTRACT

The present invention relates to a process for the preparation of oligomeric polyisocyanates in which
(a) a portion of the isocyanate groups of organic polyisocyanates is oligomerized in the presence of catalysts that accelerate the dimerization of isocyanate groups, and
(b) the oligomerization reaction is terminated after reaction of about 5 to about 45% of the isocyanate groups present in said organic polyisocyanates by the addition of a catalyst poison comprising a silylated acid corresponding to the formula $$X-[Si(CH_3)_3]_n$$

wherein
X represents the neutral acid residue obtained by removal of the acidic hydrogen atoms from an n-basic acid having a p$K_a$ value of at most 3, other than a hydrohalic acid, and
n is an integer of 1 to 3.

The invention also relates to the use of oligomeric polyisocyanates obtained by this process, optionally in admixture with unreacted starting polyisocyanates and/or optionally with the isocyanate groups blocked by blocking agents, as polyisocyanate component for the preparation of polyurethane resins by the isocyanate polyaddition process.

9 Claims, No Drawings

PROCESS FOR THE PREPARATION OF OLIGOMERIC POLYISOCYANATES AND THEIR USE

BACKGROUND OF THE INVENTION

This invention relates to a new process for the preparation of oligomeric polyisocyanates by the oligomerization of a portion of the isocyanate groups of organic polyisocyanates, followed by termination of the reaction with certain silylated acids. The invention further relates to the use of the products of the process (optionally with their isocyanate groups blocked by blocking agents) as polyisocyanate component for the production of polyurethane resins.

The term "oligomeric polyisocyanates" is used in the context of this invention to denote polyisocyanates containing uretdione groups and optional isocyanurate and/or urethane groups obtained from the catalytic dimerization of organic polyisocyanates (preferably diisocyanates) optionally in the presence of alcohol co-catalysts. The urethane groups are formed by the reaction of a portion of the isocyanate groups with the alcohol co-catalysts. Whether the reaction results mainly in dimerization products containing uretdione groups or mainly in trimerization products containing isocyanurate groups depends mainly on the degree of conversion and the temperature control, especially when using tertiary phosphines, which are preferred catalysts. See A. Farkas and G. A. Mills, *Adv. Catal.* 13, pages 393 et seq (1962).

For reproducible large scale industrial production it is, however, essential to terminate the dimerization and/or trimerization reaction (i.e. the "oligomerization reaction") precisely and rapidly at a predetermined point.

According to German Offenlegungsschrift 3,432,081, the course of the reaction is controlled by inactivation of the catalysts by means of sulfonyl isocyanates, particularly tosyl isocyanate. Tosyl isocyanate is superior as catalyst poison to the previously known catalyst poisons discussed in German Offenlegungsschrift 3,432,081, but the adducts formed by reactions between tosyl isocyanate as catalyst poison and the catalyst are obviously still so unstable that back formation of the catalyst may take place. Therefore, it is recommended to use more than equimolar quantities of sulfonyl isocyanate. The addition of equivalent quantities of tosyl isocyanate, based on the quantity of catalyst used, is indeed insufficient for reliable stopping of the reaction, as the comparison experiment described below will show.

It was, therefore, an object of the present invention to provide a new process for the oligomerization (that is, dimerization and/or trimerization) of organic polyisocyanates, preferably diisocyanates, using catalysts known in the art, whereby the reaction can be accurately stopped at the desired degree of conversion. This problem has been solved by the process according to the invention described below.

SUMMARY OF THE INVENTION

The present invention relates to a process for the preparation of oligomeric polyisocyanates comprising
(a) oligomerizing a portion of the isocyanate groups of organic polyisocyanates in the presence of catalysts that accelerate the dimerization of isocyanate groups, and
(b) terminating the oligomerization reaction after reaction of about 5 to about 45% of the isocyanate groups present in said organic polyisocyanates by the addition of a catalyst poison comprising a silylated acid corresponding to the formula $$X-[Si(CH_3)_3]_n$$

wherein
X represents the neutral acid residue obtained by removal of the acidic hydrogen atoms from an n-basic acid having a $pK_a$ value of at most 3, other than a hydrohalic acid, and
n is an integer of 1 to 3.

The invention further relates to the use of the oligomeric polyisocyanates obtained by this process, optionally in admixture with unreacted starting polyisocyanate and/or optionally having the isocyanate groups blocked by blocking agents, as the polyisocyanate component for the preparation of polyurethane resins by the isocyanate polyaddition process.

DETAILED DESCRIPTION OF THE INVENTION

The starting materials used for the process according to the invention may be any organic polyisocyanates, preferably diisocyanates. Examples of suitable polyisocyanates include aliphatic diisocyanates such as 1,6-diisocyanatohexane ("HDI"), 1-isocyanato-3,3,5-trimethyl-5-isocyanatomethylcyclohexane ("IPDI"), 4,4'-diisocyanatodicyclohexylmethane ("HMDI"), and any mixtures of such aliphatic diisocyanates. Aromatic diisocyanates such as 2,4- and/or 2,6-diisocyanatotoluene ("TDI"), 2,2'-, 2,4'-, and/or 4,4'-diisocyanatodiphenylmethane ("MDI"), and any mixtures of such aromatic diisocyanates may also be used as starting material according to the invention.

The dimerization catalysts used according to the invention may be any dimerization catalysts known in the art, for example, the dimerization catalysts described in German Offenlegungsschriften 3,030,513, 3,432,081, 1,670,720, 3,420,114, and 3,739,549. However, the preferred dimerization catalysts of the process of the invention are tertiary phosphines, preferably aliphatic, araliphatic, or mixed aliphatic-aromatic phosphines having a molecular weight in the range of from about 76 to about 500. Examples of suitable tertiary phosphines include triethylphosphine, dibutylethylphosphine, tripropylphosphine, tri(isopropyl)phosphine, tri(tert-butyl)phosphine, tribenzylphosphine, benzyldimethylphosphine, dimethylphenyphosphine, tributylphosphine, tri(isobutyl)phosphine, triamylphosphines and trioctylphosphines. Tributylphosphine is a particularly suitable catalyst for the process of the invention.

The quantity of catalyst to be used depends on the purity of the organic isocyanate used as starting material. The quantity of catalyst required in each case is, therefore, most easily determined by a preliminary test. The quantity of catalyst is normally from about 0.1 to about 1% by weight when the isocyanate groups are aliphatically bound and from about 0.01 to about 0.1% by weight in the case of aromatically bound isocyanate groups, based on the quantity of starting polyisocyanate.

It is often useful to assist the catalytic action by means of a small quantity of urethane groups that act as co-catalysts. Such co-catalysis may be achieved, for example, by adding a small quantity of an alcohol (for example, from about 0.01 to about 1% by weight, based on the weight of the starting polyisocyanate) because the added alcohol immediately reacts with the starting isocyanate (which is present in excess) to form urethane groups. Examples of suitable potential co-catalysts of this type include methanol, ethanol, 2-ethylhexanol, and 2-ethylhexane-1,3-diol. The alcohols may be added before the catalyst is added or together with the catalyst.

The oligomerization reaction, which preferably takes place in an inert gas atmosphere, is preferably carried out solvent-free in the temperature range of from about 0° C. to about 100° C. (preferably from 20° C. to 80° C.) but may also be carried out in the presence of inert solvents, for example, hydrocarbons such as toluene, chlorobenzene, or xylene or esters such as butyl acetate.

The reaction is generally stopped at a degree of oligomerization of from about 5 to about 45% (preferably from 10 to 40%), which corresponds to product yields of about 10 to 90% by weight (preferably 20 to 80% by weight). The term "degree of oligomerization" means the percentage of isocyanate groups that react during the reaction, that is, in particular, during dimerization and optional trimerization, optionally accompanied to a minor extent by urethanization. The degree of oligomerization can be monitored during the reaction, for example, by continuously determining the refractive index or the isocyanate content of the reaction mixture.

The reaction conditions and the time of termination of the reaction in the process according to the invention are generally chosen so that the reaction products obtained are mainly dimerization products (i.e., uretdiones) of the starting polyisocyanates used as starting material, possibly with minor quantities of trimerization products (i.e., isocyanurates). As these products are generally present in a subequivalent molar quantity—the molar ratio of uretdione groups to isocyanurate groups in the products of the process of the invention is preferably at least 2:1—it would be justified to describe the reaction as a "dimerization".

An essential feature of the invention is bringing about the above-mentioned termination of the reaction by the addition of the essential catalyst poisons of the invention. These essential catalyst poisons are silylated acids corresponding to the formula

in which X and n have the meanings already mentioned above. Preferred catalyst poisons are those in which X represents the neutral acid residue of an oxygen-containing acid having n acidic hydrogen atoms and a maximum $pK_a$ value of 2 in the non-silylated form. Suitable catalyst poisons include silylated sulfonic acids, such as trifluoromethanesulfonic acid trimethylsilyl ester or methanesulfonic acid trimethylsilyl ester, and silylated esters of phosphorus-containing acids, such as phosphoric acid tris(trimethylsilyl ester) or phosphoric acid diethyl ester trimethylsilyl ester.

The quantity of catalyst poison required for the invention is generally from about 0.01 to about 2 mol (preferably from 0.5 to 1.5 mol) per mol of catalyst used. The optimum quantity of catalyst poison may be determined by a preliminary test. The catalyst poison is added in the temperature range of from about 0° C. to about 100° C. (preferably 20° C. to 80° C.).

After termination of the reaction by addition of the catalyst poison according to the invention, unreacted monomeric starting polyisocyanate may, if desired, be removed by any method of separation, such as distillation (in particular, thin-layer distillation) or extraction, or, for solids, filtration. The separated unreacted polyisocyanate may then be used again for modification without significant loss of activity. The unreacted starting polyisocyanate is often reduced down to a residual content of at most 1% by weight.

Apart from the starting isocyanate being reusable, the products according to the invention have the advantage of high storage stability and improved color values (including even colorless products).

The products of the process of the invention are valuable starting materials for the preparation of polyurethane resins by reaction of the polyisocyanate component with an isocyanate-reactive component. It is particularly preferred to use these products for the production of polyurethane lacquers and polyurethane adhesives. For this purpose they may be used in known manner, either substantially freed from excess starting polyisocyanate or in the form of solutions in excess starting polyisocyanate and, if desired, blocked with known blocking agents.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all parts and percentages are parts by weight and percentages by weight, respectively.

EXAMPLES

Example 1

Example 1 demonstrates the improved reaction-stopping effect, which is an essential feature of this invention, of trifluoromethanesulfonic acid trimethylsilyl ester compared with that of toluene-4-sulfonyl isocyanate (tosyl isocyanate).

To 840 g (5 mol) of 1,6-diisocyanatohexane ("HDI") heated to 60° C. under a nitrogen atmosphere with stirring was added 2 g of 2-ethylhexanol and 2 g of tributylphosphine (10 mmol). The reaction mixture was then stirred at 60° C. while, at the same time, the progress of the reaction was followed by measuring the increasing refractive indices. A refractive index $n_D$ (23° C.) of 1.4610 was obtained after 4 hours at 60° C. (starting value: 1.4520).

Half of the crude solution was immediately stopped with 11 g (5 mmol) of a 10% solution of trifluoromethanesulfonic acid trimethylsilyl ester in HDI (Solution A), whereas 9.9 g (5 mmol) of a 10% solution of tosyl isocyanate in HDI was added to the other half of the crude solution (Solution B).

Solution A was still stable and colorless after storage for 10 days at 60° C. ($n_D$(23° C.): 1.4610). The refractive index $n_D$ (23° C.) of Solution B had increased from 1.4610 to 1.4650 after storage for only 7 hours at 60° C. and the solution had acquired a deep yellow color.

Example 2

HDI (840 g, 5 mol) was reacted with 2 g of 2-ethylhexanol and 2.5 g of tributylphosphine (12.4 mmol) according to Example 1. A refractive index (23° C.) of 1.4663 was obtained after 6 ½ hours at 60° C. The reaction was stopped with 0.9 g (4 mmol) of trifluoromethanesulfonic acid trimethylsilyl ester and the product was freed from excess HDI (down to a residue of 0.2%) by thin layer distillation at 160° C./0.1 mbar. A clear, almost colorless polyisocyanate containing uretdione and isocyanurate groups and having an isocyanate content of 22.1% and a viscosity (23° C.) of 210 mpa.s was obtained. The yield, based on the HDI originally used in the process, was 43%. Free HDI content was 0.2%.

Example 3

A solution of 150 g (0.86 mol) of 2,4-diisocyanatotoluene in 850 g of chlorobenzene was reacted with 0.2 g (1 mmol) of tributylphosphine at 25° C. A colorless precipitate began to form after 30 minutes at 25° C. and continuously increased in quantity. After 7 hours at 25° C., the reaction was stopped with 0.1 g of trifluoromethanesulfonic acid trimethylsilyl ester (0.45 mmol). The precipitate settled overnight and the supernatant solution retained its refractive index overnight ($n_D$(23° C.): 1.5266). The precipitate was separated by suction filtration. A colorless crystalline product having the following data was obtained after drying:

Yield: 75 g (50%)
Isocyanate content: 23.4%.

What is claimed is:

1. A process for the preparation of an oligomeric polyisocyanate comprising
   (a) oligomerizing a portion of the isocyanate groups of an organic polyisocyanate in the presence of a catalyst that accelerates the dimerization of isocyanate groups, and
   (b) terminating the oligomerization reaction after reaction of 5 to 45% of the isocyanate groups present in said organic polyisocyanate by the addition of a catalyst poison comprising a silylated acid corresponding to the formula $$X-[Si(CH_3)_3]_n$$

wherein
   X represents the neutral acid residue obtained by removal of the acidic hydrogen atoms from an n-basic acid having a pK a value of at most 3, other than a hydrohalic acid, and
   n is an integer of 1 to 3.

2. A process according to claim 1 wherein the catalyst is a tertiary phosphine having a molecular weight in the range of from 76 to 500.

3. A process according to claim 1 wherein the catalyst poison is a silylated oxygen-containing acid corresponding to the formula $$X-[Si(CH_3)_3]_n$$

wherein
   X represents the neutral acid residue of an oxygen-containing acid having n acidic hydrogen atoms and a maximum $pK_a$ value of 2, and
   n is an integer of 1 to 3.

4. A process according to claim 1 wherein the catalyst poison is trifluoromethanesulfonic acid trimethylsilyl ester.

5. A process according to claim 1 wherein the organic polyisocyanate used in step (a) is 1,6-diisocyanatohexane, 1-isocyanato-3,3,5-trimethyl-5-isocyanatomethylcyclohexane, 4,4'-diisocyanatodicyclohexylmethane, or any mixture thereof.

6. A process according to claim 5 additionally comprising step
   (c) reducing the excess quantity of the organic polyisocyanate used in step (a) down to a residual content of at most 1% by weight by thin-layer distillation.

7. A process according to claim 1 wherein the organic polyisocyanate used in step (a) is one or more aromatic diisocyanates selected from the group consisting of (i) 2,4and/or 2,6-diisocyanatotoluene and (ii) 2,2'-, 2,4-, and/or 4,4'-diisocyanatodiphenylmethane.

8. In a method for preparing polyurethane resins by reaction of a polyisocyanate component and an isocyanatereactive component by the isocyanate polyaddition process, the improvement wherein the polyisocyanate component is an oligomeric polyisocyanate according to claim 1.

9. A method according to claim 8 wherein the oligomeric polyisocyanate according to claim 1 is used in admixture with an unreacted starting organic polyisocyanate and/or is blocked with a blocking agent for isocyanate groups.

* * * * *